United States Patent [19]

Friese et al.

[11] Patent Number: 5,507,174
[45] Date of Patent: Apr. 16, 1996

[54] POLAROGRAPHIC SENSOR

[75] Inventors: Karl-Hermann Friese, Leonberg; Hermann Dietz; Werner Gruenwald, both of Gerlingen, Germany

[73] Assignee: Robert Bosch GmbH, Stuttgart, Germany

[21] Appl. No.: 211,569

[22] PCT Filed: Jul. 31, 1993

[86] PCT No.: PCT/DE93/00674

§ 371 Date: Aug. 2, 1994

§ 102(e) Date: Aug. 2, 1994

[87] PCT Pub. No.: WO94/04911

PCT Pub. Date: Mar. 3, 1994

[30] Foreign Application Priority Data

Aug. 11, 1992 [DE] Germany ............................ 42 26 540.1

[51] Int. Cl.⁶ .................. G01N 27/416; G01N 27/46; G01M 15/00
[52] U.S. Cl. ................. 73/23.32; 73/116; 204/410; 204/432
[58] Field of Search ........................ 73/23.32, 116; 204/432, 425, 410

[56] References Cited

U.S. PATENT DOCUMENTS

| 4,298,573 | 11/1981 | Fujishiro | 422/94 |
| 4,574,627 | 3/1986 | Sakurai et al. | 73/116 |
| 4,601,273 | 7/1986 | Kitahara et al. | 123/440 |
| 5,098,549 | 3/1992 | Friese et al. | 204/425 |
| 5,231,864 | 8/1993 | Ishida et al. | 73/23.32 |
| 5,310,472 | 5/1994 | Dietz et al. | 204/425 |
| 5,314,604 | 5/1994 | Friese et al. | 204/410 |

FOREIGN PATENT DOCUMENTS

| 0019731 | 12/1980 | European Pat. Off. . |
| 0020938 | 1/1981 | European Pat. Off. . |
| 0152942 | 8/1985 | European Pat. Off. . |
| 0194082 | 9/1986 | European Pat. Off. . |
| 0259175 | 3/1988 | European Pat. Off. . |
| 3021745 | 12/1980 | Germany . |
| 3108305 | 9/1982 | Germany . |
| 3744206 | 8/1988 | Germany . |
| 4004172 | 8/1990 | Germany . |
| 90/04171 | 4/1990 | WIPO . |

*Primary Examiner*—Hezron E. Williams
*Assistant Examiner*—J. David Wiggins
*Attorney, Agent, or Firm*—Spencer & Frank

[57] ABSTRACT

A polarographic sensor for determining concentration of certain components including oxygen or combustible fractions, such as hydrocarbons, hydrogen and carbon monoxide, in the exhaust gas of an internal combustion engine, includes a pump cell having an anode, a cathode, and an oxygen ion-conducting solid electrolyte provided between the anode and the cathode, wherein the cathode is provided with a diffusion barrier, wherein the anode is provided with a diffusion barrier, and wherein the concentration of the certain components is determined by measurement of a limiting current through the electrolyte and across one of the diffusion barriers to the corresponding anode or cathode.

7 Claims, 2 Drawing Sheets

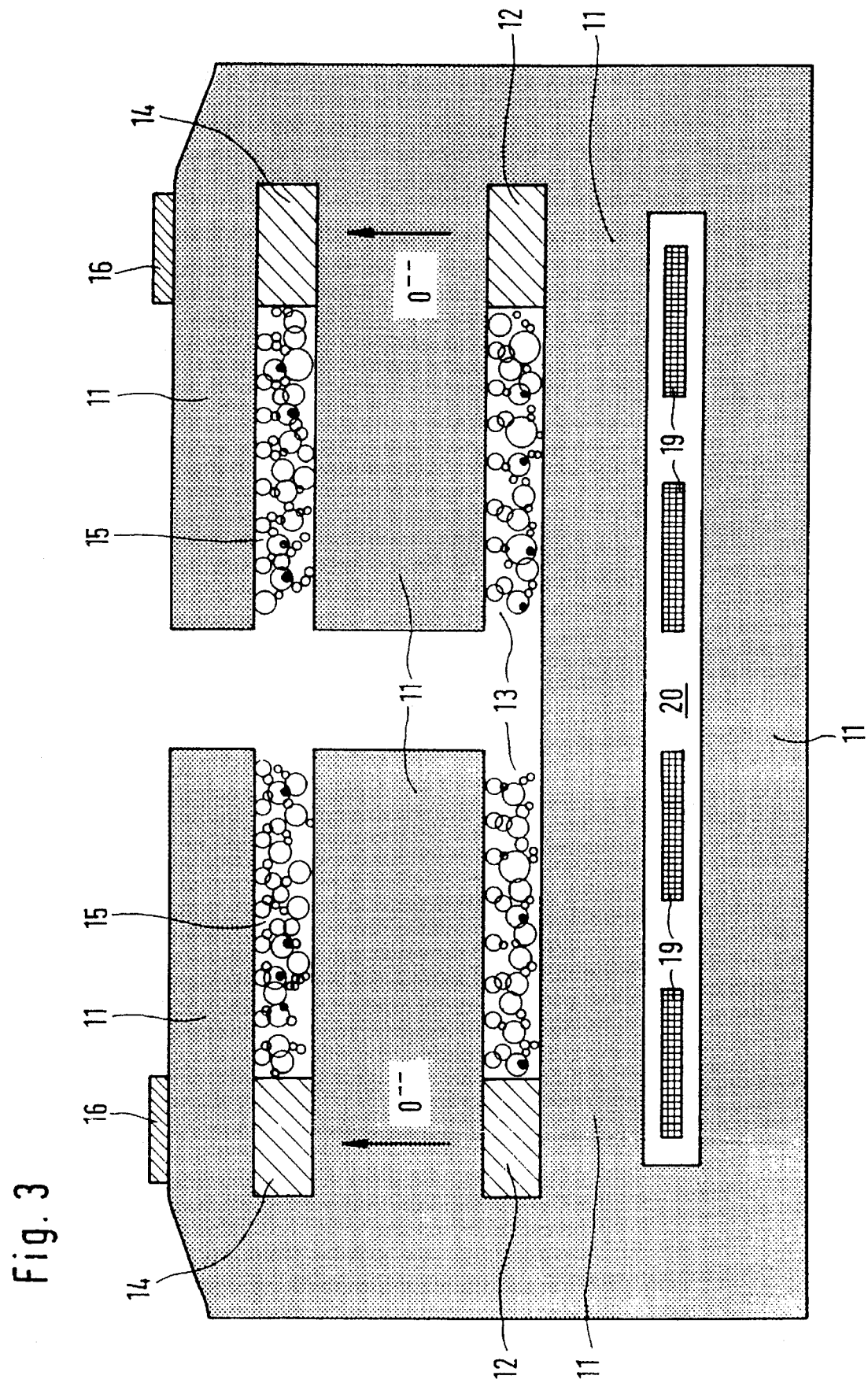

POLAROGRAPHIC SENSOR

BACKGROUND OF THE INVENTION

It is known that the concentration of certain components in gas mixtures can be determined by means of polarographic sensors. This is done, for example, in the case of exhaust gases of internal-combustion engines which are run using gaseous or liquid fuels, such as otto engines or diesel engines. It is desirable to know the content, in the exhaust gas, of oxygen and/or combustible components such as hydrogen, hydrocarbons and carbon monoxide, because these values permit inferences concerning the operational state of the engine, i.e. make it possible to distinguish between an operating mode with "lean" or "rich" air-fuel mixes.

The knowledge of the operational state forms the basis for controlling interventions for the purpose of optimizing, in a particular case, the composition of the air-fuel mix. In lean air-fuel mixes, oxygen is present in a stoichiometric excess, and accordingly, significant concentrations of oxygen are measured in the exhaust gas, while combustible components occur, if at all, in minor amounts. The opposite is the case if the engine is run on rich air-fuel mixes. In that case, considerable amounts of combustible components are still present in the exhaust gas, while oxygen occurs, if at all, at a minor concentration. A numerical measure for distinguishing between lean and rich mixes is the lambda ($\lambda$) number which represents equivalent ratio of oxygen to combustible fractions. It is >1 in lean mixes, <1 in rich mixes and =1 if oxygen and combustible components are present in a stoichiometric ratio, which is what is generally aimed for.

Polarographic probes are based on measuring the limiting current of a pump cell. In order to measure oxygen in exhaust gases from lean mixes ("lean exhaust gases") there is arranged, upstream of the cathode, a diffusion barrier which makes it so difficult for the oxygen to reach the cathode that even at an only moderate pump voltage all of the molecular oxygen is reduced virtually immediately to $0^{2-}$ ions which migrate through the electrolyte of the pump cell and are again discharged, at the anode, to give molecular oxygen. The current cannot be increased further by a higher pump voltage; a limiting current flows whose intensity virtually depends only on the oxygen concentration in the exhaust gas and on the characteristics of the diffusion barrier, especially on its layer thickness and porosity. If the probe is calibrated with reference gases, it is possible to establish an unambiguous relationship between the intensity of the limiting current and the oxygen concentration.

In the case of exhaust gases of rich air-fuel mixes ("rich exhaust gases") the combustible fractions, contained therein in a significant amount, are oxidized anodically. Here, too, it is possible to measure a concentration-dependent limiting current if the diffusion of the combustible fractions to the anode is impeded. This can be achieved, in conventional measuring probes, by reversing the polarity of the pump cell, i.e., interchanging anode and cathode. Therefore, only one diffusion barrier is present in front of one of the electrodes which, for measurements in lean gases, is connected as the cathode and for measurements in rich gases is connected as the anode. A drawback of these probes is that their polarity has to be reversed for the purpose of the rich-lean distinction, as this requires additional measuring and control effort. Moreover, the probes do not operate reliably immediately after a switch-over operation, because a steady state at the electrodes whose polarity has been reversed is established only after a certain time.

EP-B1-0 194 082 disclosed a sensor with two cells, which has the following elements:

(a) a pump cell with a first solid electrolyte and, disposed thereon, a first and a second porous electrode, (b) an "electrochemical sensor cell" with a second solid electrolyte and a third and fourth electrode, the third electrode being disposed close to the first electrode of the pump cell, (c) a diffusion resistance which impedes access of the gas to be measured to the first and third electrode, (d) a device for applying a pump current between the first and the second electrode of the pump cell, (e) a device for measuring the potential difference (or electromotive force) between the third and the fourth electrode of the "electrochemical sensor cell", and finally (f) a device for applying an auxiliary pump current between the third electrode of the "electrochemical sensor cell" and another electrode.

This sensor, of complicated design, thus emits (see feature (e)) a control signal determined potentiometrically. Moreover, the transition between rich and lean requires an electrode polarity reversal, with the same drawbacks as described previously.

SUMMARY OF THE INVENTION

The drawbacks of the sensors of the prior art are avoided by the polarographic sensors having the features of the instant invention described below when used in combination with an internal combustion engine during a control process that regulates the ratio of components for an air-fuel mixture into such engine. They require only two or three connections, respectively, for the electrical analysis of the signals, and in other respects, too, are of simple and expedient construction. They respond promptly to changes in the composition of the exhaust gas and work reliably in the temperature ranges normally used for the exhaust-gas measurement in internal-combustion engines. The embodiment of such a polyarographic sensor as described above, but additionally having an unloaded reference electrode exposed to the gas to be analyzed for the purpose of measuring the electrical polarization of the cathode or anode with respect to the reference electrode, is suitable as a wide-band sensor, i.e., for measuring both in the rich and in the lean range of the exhaust gas composition. Electrode polarity reversal is not required in the case of transition between rich and lean exhaust gases, which simplifies the electrical analysis circuit. A further advantage of the sensors according to the invention is found in the fact that they can be simply fabricated in a reliable, standard technology, e.g. by a screen-printing technique.

BRIEF DESCRIPTION OF THE DRAWINGS

The FIGS. 1 to 3 show various embodiments of the polarographic sensors according to the invention, which are explained in more detail in the subsequent description. FIG. 3 shows an actual embodiment of a sensor according to the principle of FIG. 2 in cross-section.

DESCRIPTION OF THE PREFERRED EMBODIMENTS

The polarographic sensors according to the invention are suitable for determining the concentrations of oxygen and of combustible fractions such as hydrocarbons, hydrogen and, in particular, carbon monoxide in the exhaust gas of internal-combustion engines. This is effected by measuring the limiting current of a pump cell. The conventional pump cells are employed which use an ion conducting solid layer as the electrolyte, which preferably contain zirconium dioxide, and which optionally doped with other metal oxides such as yttrium oxide, magnesium oxide and ytterbium oxide. Zirconium oxide and its mixtures with the said metal oxides show ion conductivity for oxygen at temperatures ranging from approximately 300° C. and above. The sensors according to the invention are accordingly advantageously operated at temperatures between approximately 450° and 800° C. Cathode and anode consist of the conventional metallic materials, which generally have catalytic activity, e.g. of platinum.

It is an important feature of the sensors according to the invention that both the cathode and the anode are provided with a diffusion barrier. The diffusion barrier at the cathode impedes or delays, in the case of exhaust gases of air-fuel mixes with $\lambda>1$ (lean exhaust gases), the access of oxygen to the cathode. As a result, even at a moderate pump voltage of <1 V, for example of 0.8 V, a (cathodic) limiting current is established, corresponding to the equations $$O = 4e \rightarrow 2\ O^{2-}, \quad \text{(cathode)}$$

$$2^2O^{2-} \rightarrow O_2 + 4e, \quad \text{(anode)}$$

The diffusion barrier at the anode impedes the access of combustible fractions, such as hydrocarbons, hydrogen and, in particular, carbon monoxide, to the anode, if the combustion engine is operated with air-fuel mixes with $\lambda<1$, i.e. rich exhaust gases are generated. Thus an (anodic) limiting current arises, corresponding to the equations $$CO + 2e \rightarrow CO + O^{2-} \quad \text{(Cathode)}$$

$$CO^2 + O^{2-} \rightarrow CO_2 + 2e \quad \text{(anode)}$$

A precondition for an anodic limiting current arising is that the concentration of the oxidizable components carbon monoxide, hydrogen and hydrocarbons should be considerably smaller than that of the reducible components water and carbon dioxide. This is always the case in exhaust gases of internal-combustion engines, however.

Figure 1:
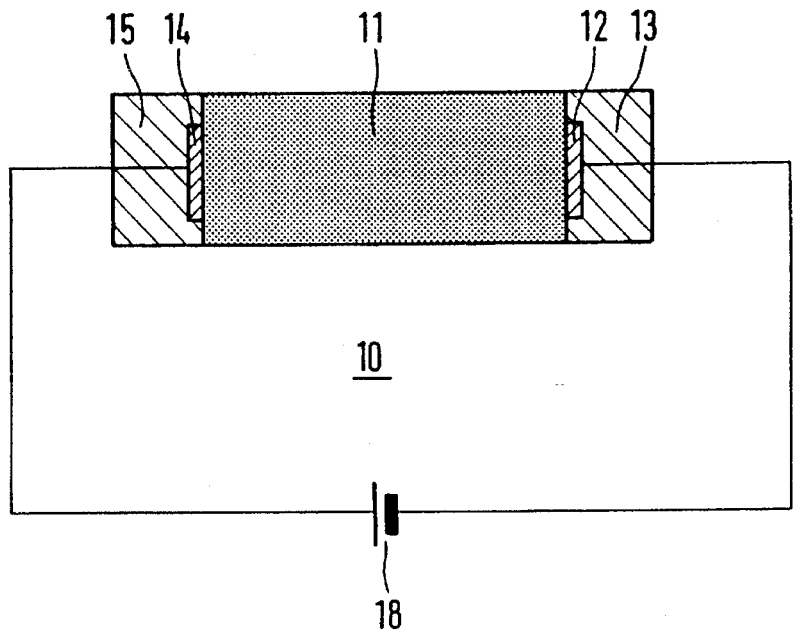
FIG. 1 shows the principle of a sensor which is preferably suitable for controlling engines which, in the normal case, operate in lean mode ($\lambda$>1), e.g., diesel engines.

FIG. 1 shows the principle of a polarographic sensor in operation to determine the concentration of certain components in the exhaust gas of an internal combustion engine. The pump cell 10 contains the electrolyte 11 and the cathode 12 with the diffusion barrier 13 and the anode 14 with the diffusion barrier 15. The direct-current source 18 supplies the required pump voltage of, as a rule, approximately 1 V. A sensor of this type is particularly suitable for use in the control of engines which, as a rule, are operated in the lean range, as is the case for diesel engines. When diesel engines are run at full load, however, it may happen that the limit $\lambda=1$ is reached or, inadvertently, briefly breached in a downward direction (less than 1). In conventional lean-limiting-current probes there is produced, in the range of rich exhaust gases, a marked increase in current, which prompts the controller to change the composition of the air-fuel mix to even lower $\lambda$ values, i.e. further towards even richer mixes. This results in strong sooting in the exhaust gas. The cause of the marked increase in current is the potential setting (or polarization) at the electrodes 12 and 14. In the rich exhaust gas, oxygen is no longer generated at the anode but instead, as described above, carbon monoxide is oxidized to form carbon dioxide (with a low overpotential). In the process, the potential of the cathode is lowered into ranges sufficiently low for electron conductivity to arise in the zirconium dioxide. This causes the marked increase in current as soon as A drops below the point $\lambda=1$. The diffusion barrier 15 according to the invention prevents the cathode potential from dropping. At the anode, a limiting current of the anodic carbon monoxide oxidation is established which takes up most of the operating voltage applied. The cathode therefore does not move into the range of significant electron conductivity, so that the marked increase in current mentioned above does not take place. Thus the diffusion barrier 15 prevents, in the case of a lean probe, incorrect controller action when the point $\lambda=1$ is reached and is inadvertently breached in a downward direction.

Figure 2:
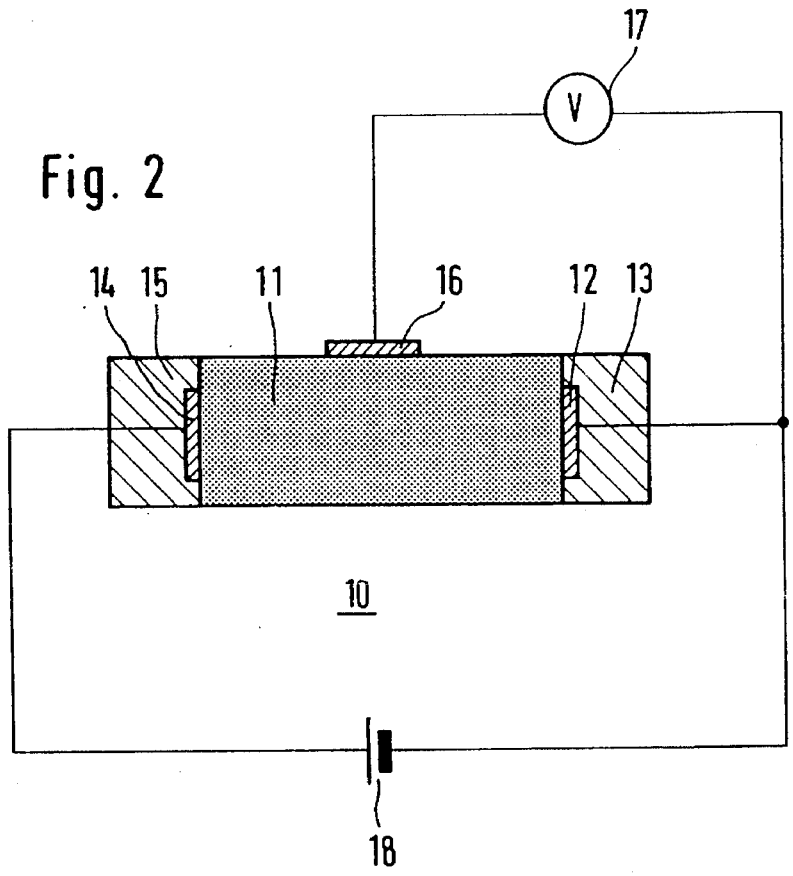
FIG. 2 depicts the principle of a wide-band sensor which can be used for installing engines both in the lean and in the rich range.

An arrangement according to the principle of FIG. 2 is preferably suitable as a wide-band sensor, that is for controlling internal-combustion engines which, as required, can be operated both in the lean and in the rich range. The arrangement differs from the sensor according to FIG. 1 inasmuch as an unloaded reference electrode 16 is provided which is preferably arranged on the electrolyte 11. The reference electrode serves for distinguishing rich and lean exhaust gases. The constant pump voltage U, which is used to operate the sensor, is made up of the polarization of the anode $P_A$, the polarization of the cathode $P_c$ and the ohmic voltage drop IR in the electrolyte:

$$U = P_A + P_c + IR$$

Owing to the high conductivity of the electrolyte 11 at the high operating temperatures of from approximately 500 to approximately 800° C., the last term is negligible in practice.

In the case of a limiting current, the polarization at the electrode determining the limiting current is greater than at the counterelectrode free of limiting current. In the lean exhaust gas, accordingly, $P_c > P_A$, as a cathodic limiting current arises. In the rich exhaust gas, in contrast, $P_A > P_c$, since in that case the limiting current at the anode determines the current flow. If the electrode polarization is measured against the unloaded reference electrode 16 by means of the voltmeter 17, a high reference voltage of the cathode 12 means that a cathodic limiting current determined by oxygen diffusion, and thus a lean exhaust gas, is present. A low reference voltage of the cathode with respect to the reference electrode, on the other hand, indicates an anodic limiting current, determined by the diffusion of combustible fractions, and thus a rich exhaust gas. Conditions are reversed if, in a manner different from that shown in FIG. 2, the reference voltages are measured between the anode 14 and the reference electrode 16. In that case, a cathodic limiting current (lean exhaust gas) is recognized by a low, and an anodic limiting current (rich exhaust gas) by a high, reference voltage of the anode 14. At $\lambda=1$, the current flow is virtually zero, and the cell voltage is made up approximately evenly of the electrode polarizations $P_A$ and $P_c$.

FIG. 3 depicts, in cross-section, an actual embodiment of a wide-band sensor according to the invention. All the elements are embedded in the continuous electrolyte 11, although the latter may optionally be fabricated in a plurality of stages. The cathode 12 and the anode 14 are expediently of annular shape, the associated diffusion barriers 13 and 15 are flat cylindrical diffusion gaps which are filled with conventional porous ceramic compositions which impede the access of the gases in question to the electrodes 12 and 14. Positioned in the gas to be analysed there is the reference electrode 16 which may likewise be annular, but may alternatively be of any other shape required. The heater 19, which is separated from the electrolyte 11 by the insulation 20, heats the electrolyte to the optimal operating temperatures of from approximately 700° to approximately 800° C. The reference electrode 16 and the cathode 12 (or anode 14) are connected to a voltmeter which is not shown. Likewise not shown is the power source 18 which supplies the pump voltage.

What is claimed is:

1. A polarographic sensor for determining concentration of certain components including oxygen or combustible fractions, such as hydrocarbons, hydrogen and carbon monoxide, in the exhaust gas of an internal combustion engine, comprising:

a pump cell having an anode, a cathode, and an oxygen ion-conducting solid electrolyte provided between the anode and the cathode, wherein the cathode is provided with a diffusion barrier, wherein the anode is provided with a diffusion barrier, and wherein the concentration of the certain components is determined by measurement of a limiting current through the electrolyte and across one of the diffusion barriers to the corresponding anode or cathode.

2. A polarographic sensor according to claim 1, further comprising an unloaded reference electrode provided on a surface of the polarographic sensor so as to maintain contact with the exhaust gas to be analyzed for measuring the electrical polarization of at least one of said cathode and anode with respect to said reference electrode, whereby the polarographic sensor operates as a wide band polarographic sensor for making measurements of the certain components in both rich and lean ranges of exhaust gas or air-fuel mixtures.

3. In combination with an internal combustion engine, an apparatus comprising a polarographic sensor according to claim 4 for regulating the ratio of the components of an air-fuel mixture supplied to the internal combustion engine.

4. In combination with an internal combustion engine, an apparatus comprising a polarographic sensor according to claim 5 for regulating the ratio of the components of an air-fuel mixture supplied to the internal combustion engine.

5. In a method of regulating the ratio of the components of an air-fuel mixture supplied to an internal combustion engine, the step of regulating the mixture by a polarographic sensor as defined in claim 1.

6. In a method of regulating the ratio of the components of an air-fuel mixture supplied to an internal combustion engine, the step of regulating the mixture by a polarographic sensor as defined in claim 2.

7. The polarographic sensor according to claim 1, wherein the limiting current has a value which depends only on porosity and thickness of the respective diffusion barriers and on the concentration of the certain components in the exhaust gas exposed to the respective diffusion barriers.

\* \* \* \* \*